United States Patent [19]

Fex et al.

[11] 4,029,778

[45] June 14, 1977

[54] CORTICAL STEROID NITROGEN MUSTARD COMPOSITIONS AND TREATMENT THEREWITH

[75] Inventors: Hans Jacob Fex; Knut Bertil Högberg, both of Helsingborg; Imre Konyves, Hittarp, all of Sweden

[73] Assignee: Aktiebolaget Leo, Helsingborg, Sweden

[22] Filed: Mar. 13, 1973

[21] Appl. No.: 335,761

Related U.S. Application Data

[62] Division of Ser. No. 4,067, Jan. 19, 1970, Pat. No. 3,732,260.

[30] Foreign Application Priority Data

Jan. 23, 1969 United Kingdom ............... 3952/69

[52] U.S. Cl. .............................................. 424/243
[51] Int. Cl.$^2$ ...................................... A61K 31/56
[58] Field of Search ..................................... 424/243

[56] References Cited

UNITED STATES PATENTS

| | | | |
|---|---|---|---|
| 2,983,649 | 5/1961 | Ercoli | 424/243 |
| 3,073,743 | 1/1963 | Spero | 424/243 |
| 3,083,197 | 3/1963 | Brown et al. | 424/243 |
| 3,484,436 | 12/1969 | Cross et al. | 260/239.55 |
| 3,649,622 | 3/1972 | Epuran | 260/239.55 |

*Primary Examiner*—Jerome D. Goldberg
*Attorney, Agent, or Firm*—Gordon W. Hueschen

[57] ABSTRACT

New 21-esters of corticoid steroid hormones, the esters having an antitumor activity, are prepared by reacting a reactive derivative of the general formula

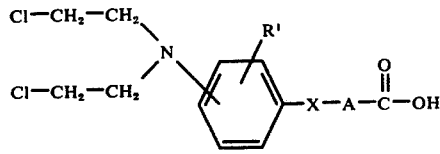

wherein $R^1$ can be hydrogen, lower alkyl, halogen, or lower alkoxy, X can be oxygen, sulphur, or a monovalent carbon-to-carbon bond, A can be alkylene, aminoalkylene, or lower-alkanoyl aminoalkylene, and A together with X also can be a monovalent carbon-to-carbon bond, with a corticoid steroid.

32 Claims, No Drawings

CORTICAL STEROID NITROGEN MUSTARD COMPOSITIONS AND TREATMENT THEREWITH

REFERENCE TO RELATED APPLICATIONS

This application is a division of our U.S. Ser. No. 4,067, filed Jan. 19, 1970, now U.S. Pat. 3,732,260, issued May 8, 1973, which parent application claims priority dating from British application Ser. No. 3952/69 of Jan. 23, 1969. This application is filed in response to a Restriction Requirement in the parent application dated Mar. 11, 1971 and made final on June 7, 1971, and is accordingly entitled to the benefits of 35 USC 121.

BACKGROUND OF THE INVENTION

It is known that corticoid steroids are effective on different animal tumors. It is also known that chlorambucil, melphalan and sarcolysin have the same effect. By esterification of corticoid steroids with acids of said types it has now been shown that the products so obtained have an effect which is far superior to that prior known.

It is an object of the present invention to provide compounds of nitrogen mustard type which are sufficiently non-toxic to be administered, for example, orally or by intramuscular or intraperitoneal injections.

SUMMARY OF THE INVENTION

The new corticoid steroid 21-esters of the present invention correspond to the general formula

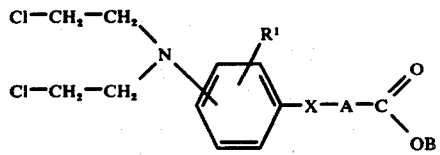

wherein $R^1$ represents hydrogen, lower alkyl, halogen or lower alkoxy,

X represents oxygen, sulphur or a monovalent carbon-carbon bond,

A represents the alkylene group

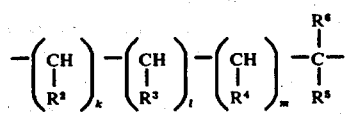

wherein $R^2$, $R^3$, $R^4$, $R^5$ and $R^6$ represent similar or dissimilar atoms or atom groups selected from the class consisting of hydrogen and lower alkyl, and wherein $R^6$ may also be selected from amino and lower-alkanoyl amino in which case $R^5$ must be hydrogen, wherein $k$, $l$ and $m$ are zero or one, or A together with X (—X—A—) represent a monovalent carbon-carbon bond, and B represents a corticoid steroid hormone, the point of attachment being its 21-position, and acid addition salts of compounds wherein $R^6$ is amino.

The group $(ClCH_2CH_2)_2N$— in the above compounds is most preferably in the para or metaposition with regard to X.

The term "lower alkyl" is used herein as meaning as alkyl group containing a maximum of 4 carbon atoms. The terms "lower alkoxy" and "lower-alkanoyl" are used herein as meaning an alkoxy or alkanoyl group containing a maximum of 4 carbon atoms.

The esters of the invention have shown effect in inhibiting the growth of several tumors, e.g., Ehrlich ascites, Hepatoma AH 130, lymphocytic leukemia (L1210), Walker 256 and Harding-Passey Melanoma according to the procedure of Cancer Chemotherapy National Service Center (Ref.: Cancer Chemotherapy Reports, December 1962).

The compounds of the invention can be employed in disorders responsive to treatment with anticancer agents and with immunosuppressive agents as such or combined with either solid or liquid carriers or diluents and made available in varying amounts in such pharmaceutical forms as tablets, capsules, powders and aqueous or nonaqueous suspensions and solutions.

DESCRIPTION OF THE PREFERRED EMBODIMENTS

The compounds of the present invention as defined by the general formula (I) may be prepared by reacting a reactive derivative of a compound of the general formula:

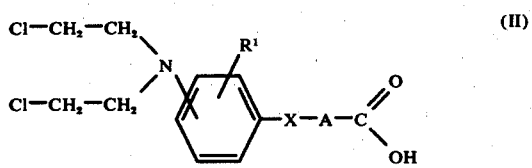

wherein the symbols have the meanings previously assigned, with a 21-hydroxy corticoid steroid or a reactive 21-ester derivative thereof in known manner, each group of the compounds involved being compatible with the procedure employed or protected if necessary so that a compound of the general formula (I) is obtained.

Such starting corticoid steroids can be pregn-4-en-17α21-diol-3,11,20-trion(cortisone); pregn-4-en-11β, 17α, 21-triol-3,20-dion(hydrocortisone); pregn-4-en-11β, 21-diol-3,20-dion(corticosterone); pregn-4-en-21-ol-3,11,20-trion-(dehydrocorticosterone); pregna-1,4-dien-17α, 21-diol-3,11,20-trion-(prednisone); pregna-1,4-dien-11β, 17α, 21-triol-3,20-dion-(prednisolone); 6α-methyl-pregna-1,4-dien-11β, 17α, 21-triol-3,20-dion(6α-methylprednisolone); 9α-fluor-pregn-4-en-11β, 17α, 21-triol-3,20-dion(9α-fluorhydrocortisone); 6α,9α-difluor-pregn-1,4-dien-11β, 16α, 17α, 21-tetrol-3,20-dion(6α, 9α-difluoro-16α-hydroxy prednisolone); 16α-methyl-9α-fluor-pregna-1,4-dien-11β, 17α, 21-triol-3,20-dion(16α-methyl-9α-fluor-prednisolone); 9α-fluor-16β-methylprednisonole; 9α-fluor-16α-hydroxyprednisolone; 16-methylenprednisolone; 6α, 9α-di-fluor-11β, 17α, 21-trihydroxy-16α-methylpregnadien-(1,4)-dion-(3,20) (6α,9α-difluor-16α-methylprednisolone); 6α,9α-difluor-11β, 21-dihydroxy-3,20-dioxo-16α,17α-isopropyliden-dioxypregnadien-(1,4); 6α,9α-difluor-16α-hydroxyprednisoloneacetonid-(16,17); 6α-fluor-11β, 21-dihydroxy-16α-methyl-3,20-dioxopregnadien-(1,4); 6α-fluor-16α-hydroxyhydrocortisone-16,17-acetonid; and 6α-fluor-16α-methylprednisolone.

The compounds of general formula (II) which have one or more asymmetric carbon atoms may exist in different possible stereoisomeric forms and the present invention includes such stereoisomers and also the racemates of such compounds.

The process of the invention, then, involves reaction of a reactive derivative of a compound of formula (II), with a 21-hydroxy corticoid steroid or a reactive ester derivative thereof. Such procedure advantageously involves reaction of the 21-hydroxy corticoid steroid with (II) in the form of its acid halide, e.g., the chloride or bromide, or its acid anhydride, or in the form of a mixed anhydride of (II) with another acid, e.g., a lower aliphatic acid such as a lower-alkanoic acid, e.g., acetic acid. These reactions may be conducted in a solvent, e.g., pyridine, and at room temperature or there about. Alternatively, where slightly less mild reaction conditions are desired, or permissible, e.g., a temperature of up to about 60° C., e.g., 45° C., and a reaction period up to about two days or so, a reactive ester of the starting 21-hydroxycorticoid steroid, e.g., the tosylate, methylsulfonate (mesylate), iodide, bromide, or chloride, may be employed. These may be reacted, in the alternative procedure, with (II) in the form of an alkali metal salt, e.g., the sodium or potassium salt. The solvent in such case may advantageously be dimethylsulfoxide, dimethylformamide, acetone, or the like. Such alternative procedure is especially recommended where amino or lower-alkanoylamino end products are desired.

Alternatively, sensitive groups in either the 21-hydroxysteroid molecule or in (II) or its reactive derivative can be protected during reaction and the protecting group removed there after according to conventional procedure to restore the sensitive group, e.g., hydroxy groups in the steroid molecule and an amine group $R^6$ in (II). For example, sensitive steroid hydroxy groups may be protected during the 21-esterification reaction by converting to a protecting group which is reconvertible to hydroxy in known manner, as by hydrolysis, for example, one of the conventional protective groups such as ketal, acetal, or lower-alkanoyloxy such as formyloxy or acetyloxy. In addition, or independently, the $R^6$ group, if it is to appear in the final product as the free amino group, or an acid addition salt thereof, can be protected in known manner during the 21-esterification reaction by conversion to a selected protective group which is readily reconverted to an amino group in any of various convenient known ways. For example, such representative protected $R^6$ groups include benzyloxycarbonylamino or parachloro, methoxy, or nitro derivatives thereof, t-butoxycarbonylamino, tritylamino, trifluoroacetylamino, and formylamino. In addition, this formyl group or other lower-alkanoylamino groups may be used either as $R^6$ protected groups or they may be left in the ultimate product as they do not appear to detract from the antitumor activity when present in the products of formula (I). However, when $R^6$=amino or lower-alkanoylamino compounds are desired, these may also be advantageously obtained using relatively mild conditions by the anhydride and the steroid 21-alcohol or the acid potassium salt and the steroid 21-tosylate.

For therapeutic purposes the $R^6$ amino bases of the general formula (I) may be employed as such or in the form of acid addition salts containing anions which are pharmaceutically acceptable, such as hydrochlorides, hydrobromides, phosphates, nitrates, sulphates, hydrogenoxalates, oxalates, succinates, tartrates, methanesulphonates and ethandisulphonates, so that the beneficial physiological properties are not vitiated by side-effects ascribable to the anions.

The compounds of the invention are generally characterized by the pharmacological activity hereinbefore stated, making them useful in counteracting certain physiological abnormalities in a living animal body. Effective quantities of the pharmacologically active compounds of the invention may be adminstered to a living animal body in any one of various ways or modes, for example, orally as in capsules or tablets, or parenterally in the form of sterile solutions, suspensions, or by pellet implantation, and in some cases intravenously in the form of sterile solutions. Other modes of administration are cutaneously, subcutaneously, bucally, intramuscularly, and intraperitoneally.

As representative of living animal bodies which may be treated with the compounds and compositions of the invention, and according to the method of treating of the invention, for alleviation of the same and/or similar conditions are those described, in addition may also be mentioned the following: domestic animals such as dogs and cats, farm animals such as horses, cows, sheep and goats.

Pharmaceutical formulations are usually prepared from a predetermined quantity of one or more of the compounds of the invention. Such formulations may take the form of powders, elixirs, solutions, pills, capsules, pellets or tablets, suspensions, oil solutions etc., with or without, but preferably with, any one of a large variety of pharmaceutically acceptable vehicles or carriers. When in admixture with a pharmaceutical vehicle or carrier, the active ingredient usually comprises from about 0.01 to about 75 percent, normally from about 0.05 to about 15 percent, by weight of the composition. Carriers such as starch, sugar, talc, commonly used synthetic and natural gums, water, and the like, may be used in such formulations. Binders such as polyvinylpyrrolidone and lubricants such as sodium stearate, may be used to form tablets. Disintegrating agents such as sodium bicarbonate may also be included in tablets.

Although relatively small quantities of the active materials of the invention, even as low as 5.0 milligram, may be used in cases of administration to subjects having a relatively low body weight, unit dosages are preferably 5 milligrams or above and preferably 25, 50, or 100 milligrams, or even higher, depending of course upon the subject treated and the particular result desired, as will be apparent to one skilled in the art. Broader ranges appear to be 1 to 3,000 milligrams per unit dose. The active agents of the invention may be combined for administration with other pharmacologically active agents, such as analgesics, tranquillizers, steroids or hormones, or the like, or with buffers, antacids or the like, and the proportion of the active agent or agents in the compositions may be varied widely. It is only necessary that the active ingredient of the invention constitutes an effective amount, i.e., such that a suitable effective dosage will be obtained consistent with the dosage form employed. Obviously, several unit dosage forms may be administered at about the same time. The exact individual dosages as well as daily dosages in a particular case will of course be determined according to well established medical and/or veterinary principles. As a rule, however, when used therapeutically, the present compounds may be administered in a quantity of 10 to 1000 milligrams per day and patient, divided in 1 to 4 doses, during a period of 1 day to 1 year. Dosages of 2 to 100 mg. daily, and especially 2 to 50 mg. daily, are preferred.

The following examples are intended to illustrate but not to limit the scope of the present invention.

EXAMPLE 1

A solution of 12.5 g p-/N-bis(β-chloroethyl)-amino/-benzoylchloride in 135 ml dry pyridine was added slowly with stirring and under anhydrous conditions, to a solution of 12.5 g hydrocortisone in 120 ml dry pyridine which was cooled in an ice bath. The reaction mixture was then kept at room temperature for 40–50 hours after which the excess of acid chlorides was hydrolyzed with crushed ice and the resulting solution was poured into a mixture of conc HCl and crushed ice.

The precipitate was collected and dissolved in 500 ml ethyl acetate. This solution was washed several times with cold 1.0-N NaHCO$_3$ and finally water. After drying over anhydrous sodium sulphate the solvent was removed in vacuo.

The residue is the hydrocortisone-21-p-/N-bis (β-chloroethyl)-amino/-benzoate which after crystallization from acetone had a melting point of 156°–8° C.

$(\alpha)_D^{24}$ $^c = 212°$ (c = 1.00 in chloroform)

EXAMPLE 2

A solution of 3.4 g p-/N-bis(β-chloroethyl)-amino/-benzoyl chloride in 50 ml dry tetrahydrofuran was added slowly, with stirring and under anhydrous conditions to a solution of 3.6 g hydrocortisone in 50 ml dry tetrahydrofuran which was cooled in an ice bath. The reaction mixture was kept at room temperature for 70 hours after which the excess of acid chloride was hydrolyzed with crushed ice and the resulting solution was poured into a mixture of conc. HC1 and crushed ice and extracted with 200 ml ethyl acetate. The ethyl acetate solution was washed several times with cold 1.0-N NaHCO$_3$ and finally water.

After drying over anhydrous sodium sulphate the solvent was removed in vacuo.

The residue is the hydrocortisone-21-p-/N-bis(β-chloroethyl)-amino/-benzoate which after crystallization from acetone had the same data as mentioned in Example 1.

EXAMPLE 3

According to the same procedure as in Example 1, cortisone-21p-/N-bis(β-chloroethyl)-amino/-benzoate was obtained from 4.5 g cortisone and 5.65 g p-/N-bis(β-chloroethyl)-amino/-benzoyl chloride.

After crystallization from chloroform-hexane the compound had a m.p. of 228°–31° C.

$(\alpha)_D^{24}$ $^c = 186°$ (c = 1.03 in chloroform)

EXAMPLE 4

According to the same procedure as in Example 1, prednisone-21-p-/N-bis(β-chloroethyl)-amino/-benzoate was obtained from 11.8 g prednisone and 11.8 g p-/N-bis(β-chloroethyl)-amino/-benzoyl chloride.

After crystallization from ethanol the compound had a m.p. of 214°–6° C.

$(\alpha)_D^{24}$ $^c = 216°$ (c = 1.05 in chloroform)

EXAMPLE 5

According to the same procedure as in Example 1, prednisolone-21-p-/N-bis(β-chloroethyl)-amino/-benzoate was obtained from 12.5 g prednisolone and 12.5 g p-/N-bis(β-chloroethyl)-amino/-benzoyl chloride.

After crystallization from acetone-hexane the compound had a m.p. of 198°–201° C.

$(\alpha)_D^{24}$ $^c = 204°$ (c = 1.04 in chloroform)

In the same manner as above but using 4-/N-bis(β-chloroethyl)-amino/-2-chloro-benzoyl chloride, 4-/N-bis(β-chloroethyl)-amino/-3-methoxy-benzoyl chloride and 4-/N-bis(β-chloroethyl)-amino/-3-methyl-benzoyl chloride respectively the following substituted 21-benzoate of prednisolone were prepared:

prednisolone-21-4'-/N-bis(β-chloroethyl)-amino/-2'-chlorobenzoate;

prednisolone-21-4'-/N-bis(β-chloroethyl)-amino/-3'-methoxybenzoate; and prednisolone-21-4'-/N-bis(β-chloroethyl)-amino/-3-methylbenzoate.

EXAMPLE 6

According to the same procedure as in Example 1, prednisolone-21-m-/N-bis(β-chloroethyl)-amino/-benzoate was obtained from 3.0 g prednisolone and 5.0 g m-/N-bis(β-chloroethyl)-amino/-benzoyl chloride.

After crystallization from acetone-hexane the compound had a m.p. of 150°–3° C.

$(\alpha)_D^{24}$ $^c = 149°$ (c = 1.00 in chloroform)

In the same manner as above but using 3-/N-bis(β-chloroethyl)-amino/-4-methyl-benzoyl chloride the prednisolone-21-3'/N-bis-(β-chloroethyl)-amino/-4'-methyl-benzoate was prepared. (cf.Ex. 18)

EXAMPLE 7

Preparation of acid anhydrides not previously described in the literature.

These are prepared according to known methods, e.g.: 27.5, of p-/N-bis(β-chloroethyl)-amino/-phenylacetic acid was dissolved in a mixture of 150 ml dry benzene and 8.04 ml dry pyridine. The solution was cooled in an ice bath and a solution of 3.58 ml thionyl chloride in 30 ml dry benzene was slowly added with stirring under anhydrous conditions.

The reaction mixture was then kept at room temperature for 1 hour and thereafter poured into a mixture of 5.0 N HC1 and crushed ice. The benzene solution was immediately washed with water, with cold 1.0 N NaHC0$_3$ and finally with cold water. After drying over anhydrous sodium sulphate, the benzene was removed in vacuo. The residue is the p-/N-bis(β-chloroethyl)-amino/-phenylacetic anhydride which could be used without any further purification. After crystallization from ether-acetone it had a m.p. of 64° C.

EXAMPLE 8

To a solution of 27.5 g p-/N-bis(β-chloroethyl)-amino/-phenylacetic anhydride in 500 ml dry pyridine was added 17.7 g of prednisolone. The reaction mixture was kept at room temperature for 24 hours under anhydrous condition. It was then poured into a mixture of conc. HCl and crushed ice and extracted with ether-ethyl acetate (1:1).

The organic phase was washed several times with cold 1.0 N K$_2$CO$_3$ and finally water. After drying over CaCl$_2$ the solvent was removed in vacuo.

The residue is prednisolone-21-p-/N-bis(β-chloroethyl)-amino/-phenylacetate which after crystallization from methanol had a m.p. of 175°–7° C.

$(\alpha)_D^{24°}$ $^c = 86.5°$ (c = 1.02 in chloroform)

In the same manner as above but using hydrocortisone the hydrocortisone-21-p-/N-bis(β-chloroethyl)-amino/-phenylacetate was prepared.

EXAMPLE 9

According to the same procedure as in Example 8, prednisolone-21-3'-[p-/N-bis(β-chloroethyl)-amino/-phenyl]-propionate was obtained from 10.0 g prednisolone and 18.8 g 3-[p-/N-bis(β-chloroethyl)-amino/-phenyl]-propionic anhydride (prepared according to Example 7).

After crystallization from methanol-water the compound had a m.p. of 175° C.

$(\alpha)_D^{24}$  $c = 93.9°$ (c = 1.03 in chloroform)

In the same manner as above but using hydrocortisone the hydrocortisone-21-3'-[p-/N-bis(β-chloroethyl)-amino/-phenyl]-propionate was prepared.

EXAMPLE 10

According to the same procedure as in Example 8, prednisolone-21-4'-[p-/N-bis(β-chloroethyl)-amino/-phenyl]-butyrate was obtained from 24.4 g prednisolone and 42 g 4-[p-/N-bis(β-chloroethyl)-amino/-phenyl]-butyric anhydride (prepared according to Example 7).

After crystallization from methanol-water the compound had a m.p. of 163°-4° C.

$(\alpha)_D^{24}$  $c = 92.9°$ (c = 1.06 in chloroform)

In the same manner as above but using respectively cortisone, hydrocortisone and prednisone the cortisone-21-4'[p-/N-bis(β-chloroethyl)-amino/-phenyl]-butyrate, the hydrocortisone-21-4'-[p-/N-bis(β-chloroethyl)-amino/-phenyl]-butyrate and the prednisone-21-4'[p-/N-bis(β-chloroethyl)-amino/-phenyl]-butyrate were prepared.

From prednisolone and 3-[p-/N-bis(β-chloroethyl)-amino/-phenyl]-butyric anhydride (prepared according to Example 7) the prednisolone-21-3'-[p-/N-bis(β-chloroethyl)-amino/-phenyl]-butyrate and from hydrocortisone and 5-[p-/N-bis(β-chloroethyl)-amino/-phenyl]-valerianic anhydride (prepared according to Example 7) the hydrocortisone-21-5'-[p-/N-bis(β-chloroethyl)-amino/-phenyl]-valerianate were obtained in a similar way.

EXAMPLE 11

According to the same procedure as in Example 8, prednisolone-21-p-/N-bis(β-chloroethyl)-amino/-phenoxy acetate was obtained from 6 g prednisolone and 10 g p-/N-bis(β-chloroethyl)-amino/-phenoxyacetic anhydride (prepared according to Example 7).

After crystallization from methanol-water the compound had a m.p. of 177° C.

$(\alpha)_D^{24}$  $c = 98.1°$ (c = 1.04 in chloroform)

In the same manner as above but using cortisone, hydrocortisone, prednison and prednisolone respectively together with the anhydrides (prepared according to Example 7) from 3-[p-/N-bis(β-chloroethyl)-amino/-phenoxy]-propionic acid, 4-[p-/N-bis(β-chloroethyl)-amino/-phenoxy]-butyric acid and 5-[p-/N-bis(β-chloroethyl)-amino/-phenoxy]-valerianic acid the following compounds were prepared:

cortisone-21-3'-[p-/N-bis(β-chloroethyl)-amino/-phenoxy]-propionate;

hydrocortisone-21-3'-[p-/N-bis(β-chloroethyl)-amino/-phenoxy]-propionate;

prednisone-21-3'-[p-/N-bis(β-chloroethyl)-amino/-phenoxy]-propionate;

prednisolone-21-3'-[p-/N-bis(β-chloroethyl)-amino/-phenoxy]-propionate;

prednisolone-21-4'[p-/N-bis(β-chloroethyl)-amino/-phenoxy]-butyrate; and hydrocortisone-21-5'[p-/N-bis(β-chloroethyl)-amino/-phenoxy]-valerate.

EXAMPLE 12

To a solution of 20.8 g [p-/N-bis(β-chloroethyl)-amino/-phenylthio]-acetic anhydride (prepared according to Example 7) in 400 ml dry pyridine was added 11.5 g of prednisolone. A crude prednisolone-21-ester was obtained in the same manner as described in Example 8. The residue obtained after removing the solvent in vacuo was dissolved in dry benzene and the solution chromatographed on a silicagel column, eluating with benzene-acetone (9:1). The main fraction was evaporated in vacuo to dryness whereupon the residue crystallized upon triturating with hexane.

The prednisolone-21-[p-/N-bis(β-chloroethyl)-amino/-phenyl-thio]-acetate obtained had no definable melting point. The identity was confirmed by NMR and analysis for S, N and Cl.

EXAMPLE 13

A solution of 14.6 g p-/N-bis-(β-chloroethyl)-amino/-α,α-dimethyl-phenyl acetic acid in 180 ml dry benzene was added with stirring and under anhydrous conditions to 40 ml thionyl chloride, which was cooled in an ice bath, the reaction mixture was then kept at room temperature for 3-4 hours and the precipitate was removed by filtration and washed several times with benzene and dried over $P_2O_5$. This compound is p-/N-bis-(β-chloroethyl)-amino/-α,α-dimethyl-phenyl acetic chloride which could be used without any further purification.

9.8 g of this compound and 9.3 g of prednisolone was dissolved in 150 ml of dry pyridine. The solution was then kept at room temperature for 50 hours and thereafter poured into a mixture of conc. HCl and crushed ice and extracted with ether-ethylacetate (1:1).

The organic phase was washed several times with cold 1.0 N $K_2CO_3$ and finally water. After drying over sodium sulphate the solvent was removed in vacuo and the residue chromatographed on a silicagel column with a mixture of benzene-acetone-acetic acid. Evaporation in vacuo to dryness and crystallization from methanol-water gave the prednisolone-21-[p-/N-bis-(β-chloroethyl)-amino/-α,α-dimethyl]-phenyl acetate with a m.p. of 117°-9° C.

$(\alpha)_D^{24}$  $c = 69°$ (c = 1.00 in chloroform)

In the same manner as above but using prednisone the prednisone-21-[p-/N-bis-(β-chloroethyl)-amino/-α,α-dimethyl]-phenyl acetate was prepared.

EXAMPLE 14

Tablets of 10 mg

| | | |
|---|---:|---|
| Prednisolone-21-4'-[p-/N-bis-(β-chloroethyl)-amino/-phenyl]-butyrate | 10 | mg |
| Lactose | 64 | mg |
| Starch | 21.5 | mg |
| Polyvinylpyrrolidone | 1.5 | mg |
| Distilled water q.s. | | |
| Talc | 5 | mg |
| Magnesium stearate | 0.5 | mg |

The prednisolone-21-4'-[p-/N-bis-(β-chloroethyl)-amino/-phenyl]-butyrate, lactose and starch were mixed together and screened. The polyvinylpyrrolidone was dissolved in a suitable amount of water and added to said mixture, which was then granulated. The granulate obtained was then dried and mixed with the talc and the magnesium stearate, whereafter tablets were made.

EXAMPLE 15

| Pellets of 100 mg | |
|---|---|
| Prednisolone-21-p-/N-bis-(β-chloroethyl)-amino/-benzoate | 100 mg |
| Lactose | 100 mg |
| Polyvinylpyrrolidone | 4 mg |
| Distilled water q.s. | |

The prednisolone-21-p-/N-bis-(β-chloroethyl)-amino/-benzoate, lactose and polyvinylpyrrolidone were mixed and granulated, whereafter tablets were made.

EXAMPLE 16

| Aqueous suspension of 100 mg for injection | |
|---|---|
| Prednisolone-21-p-/N-bis(β-chloroethyl)-amino/-benzoate | 100 mg |
| Polyoxyethylene sorbitan monostearate (Tween 80, Atlas) | 20 mg |
| Benzyl alcohol | 45 mg |
| Carboxymethyl-cellulose | 15 mg |
| Distilled water to make | 5 ml |

The carboxy methyl-cellulose was dissolved in water. Tween 80 and benzylalcohol were dissolved in this solution, whereafter prednisolone-21-p-/N-bis(β-chloroethyl)-amino/-benzoate was added to this mixture and the suspension was made with water to 5 ml.

EXAMPLE 17

| Oil solution of 50 mg for injection | | |
|---|---|---|
| Prednisolone-21-4'-[p-/N-bis(β-chloroethyl)-amino/-phenyl]-butyrate | 50 | mg |
| Benzyl benzoate | 0.8 | g |
| Castor oil to make | 2 | mg |

Prednisolone-21-4'-[p-/N-bis(β-chloroethyl)-amino/-phenyl]-butyrate was dissolved in benzyl benzoate and this mixture was added to castor oil, whereafter the solution was dispensed and sterilized.

EXAMPLE 18

To a solution of 7 g m-N-bis-(β-chloroethyl)amino-p-toluic acid in 90 ml dry benzene was added 23 ml SOCl$_2$ dropwise with stirring. The reaction mixture was then boiled for 45 min. under anhydrous conditions.

The solution was filtered and evaporated to dryness. The remaining oil is m-N-bis-(β-chloroethyl)amino-p-toluic acid chloride which could be used without any further purification.

The compound was dissolved in 100 ml dry pyridine. 7.1 g prednisolone was added to the pyridine solution. The reactionmixture was kept at room temperature for 24 hours and thereafter poured into a mixture of conc. HCl and crushed ice.

The precipitate was filtered off, washed with water and dried.

Crystallization from acetone-hexane gave the prednisolone-21-3'-[N-bis-(β-chloroethyl)-amino]-4'-methyl-benzoate, having the desired antitumor activity.

$(\alpha)_D^{24}$  $c = +153°$ (C = 1.03 in CHCl$_3$)

In the same manner as above but using hydrocortisone the hydrocortisone-21-3'-[N-bis-(β-chloroethyl)-amino]-4'-methylbenzoate is prepared and determined to have the desired antitumor activity.

EXAMPLE 19

30.8 g prednisolone-21-p-toluenesulfonate was dissolved in 600 ml acetone and was rapidly mixed with a solution of 18.2 g 4-[p-N-bis-(β-chloroethyl)-aminophenyl]butyric acid in 600 ml acetone containing 60 ml 1.0-N methanolic KOH-solution.

The mixture was kept at +45° C. for 50 hrs, filtered and evaporated to dryness. The remaining solid was crystallized from methanol to give prednisolone-21-4'-p-[N-bis-(β-chloroethyl)-amino]-phenyl -butyrate with a m.p. of 163°–64° C.

$(\alpha)_D^{24}$  $c = 92.9°$ (C = 1.06 in CHCl$_3$)

In the same manner as above but using p-N-bis-(β-chloroethyl)-aminobenzoic acid the prednisolone-21-p-[N-bis-(β-chloroethyl)-amino]-benzoate is prepared and determined to have the desired antitumor activity.

In the same manner as above but using hydrocortisone-21-p-toluenesulfonate the hydrocortisone-21-4'-p-[N-bis-(β-chloroethyl)-amino]-phenyl -butyrate is prepared and determined to have the desired antitumor activity.

In the same manner as given above, but starting from p-[N-bis-(β-chloroethyl)-amino]-phenylalanine, and prednisolone-or hydrocortisone-21-para-toluenesulfonate, the prednisolone-21-3'- p-[N-bis-(β-chloroethyl)-amino]-phenyl -2'-aminopropionate and hydrocortisone-21-3'- p-[N-bis-(β-chloroethyl)-amino]-phenyl -2'-aminopropionate are prepared and isolated and in each case found to have the desired antitumor activity.

EXAMPLE 20

To a solution of 16.5 g the anhydride (prepared according to Example 7) from p-[N-bis-(β-chloroethyl)-amino]-N-acetyl-phenylalanine (prepared from para-N-bis-(β-chloroethyl)-aminophenylalanine using acetic anhydride) in 200 ml dry pyridine was added 7.2 g prednisolone. A crude prednisolone-21-ester was obtained in the same manner as described in Example 8. It was dissolved in dry benzene and the solution chromatographed on a silicagel column, eluating with benzene-aceton (9:1). The main fraction was evaporated in vacuo to dryness whereupon the residue crystallized upon triturating with hexane.

The prednisolone-21-3'- p-[N-bis-(β-chloroethyl)-amino]-phenyl -2'-acetamido-propionate obtained had no definable melting point. The compound is an active antitumor agent, e.g., against Walker 256 tumors. The identity was confirmed by NMR and analysis for N and Cl.

In the same manner as above but using hydrocortisone, the hydrocortisone-21-3'- p-[N-bis-(β-chloroethyl)-amino]-phenyl -2'-acetamido-propionate is prepared and found to have the same activity.

In the same manner, the N-formyl, N-propionyl, N-butyryl, and N-isobutyryl compounds are prepared and found to have the desired antitumor activity.

EXAMPLE 21 — ANIMAL EXPERIMENTS

The esters of this invention were tested for effectiveness in inhibiting the growth of Ehrlich ascites, Hepatoma 130, lymphocytic leukemia (L 1210), and Harding-Passey Melanoma, and Walker 256 tumors. The administration was by the intraperitoneal route in each case.

Some results obtained are given in Tables 1, 2, 3 and 4. Good results have also been obtained by oral administration, as shown in Table 5. The compounds also exhibit a corticoid effect upon administration, whether orally or parenterally.

Various modifications and equivalents will be apparent to one skilled in the art and may be made in the compounds, compositions and methods of the present invention without departing from the spirit or scope thereof, and it is therefore to be understood that the invention is to be limited only by the scope of the appended claims.

TABLE I

| Compound | Ehrlich ascites tumor Lethality (mg/kg) | Effect (mg/kg) | T.I.[x] |
|---|---|---|---|
| Prednisolone-21-p-[N-bis($\beta$-chloroethyl)-amino]-benzoate (I) | 1 × 1000 no toxicity | ED50 = 1 × 13 | >77 |
| Prednisone-21-p-[N-bis($\beta$-chloroethyl)-amino]-benzoate | 1 × 1000 no toxicity | ED50 = 1 × 12 | >83 |
| Hydrocortisone-21-p-[N-bis($\beta$-chloroethyl)-amino]-benzoate | LD50 > 1 × 500 | ED50 = 1 × 15 | >33 |
| Prednisolone (II) | 1 × 1000 no toxicity | ED50 = 1 × 120 | >8.3 |
| p-[N-bis($\beta$-chloroethyl)-amino]-benzoic acid (III) | LD50 = 1 × 125 | 1 × 63: no effect | <2 |
| II + III (in the same ratio as in compound I) | LD50 = 1 × (218+158) | 1 × (149+105): no effect | <1.5 |

$^{x}$T.I. = $\frac{LD50}{ED50}$

TABLE 2

| Compound | Hepatoma 130 tumor Lethality (mg/kg) | Effect (mg/kg) | T.I.[x] |
|---|---|---|---|
| Prednisolone-21-p-[N-bis($\beta$-chloroethyl)-amino]-benzoate (I) | LD50 = 1 × 420 | ED50 = 1 × 5.6 | 75 |
| Prednisone-21-p-[N-bis($\beta$-chloroethyl)-amino]-benzoate | 1 × 1000 no toxicity | ED50 = 1 × 58 | >18 |
| Hydrocortisone-21-p-[N-bis($\beta$-chloroethyl)-amino]-benzoate | LD50 > 1 × 1000 | ED50 = 1 × 28 | >36 |
| Prednisolone (II) | LD50 = 1 × 780 | ED50 = 1 × 118 | 6.6 |
| p-[N-bis($\beta$-chloroethyl)-amino]-benzoic acid (III) | LD50 = 1 × 125 | ED50 = 1 × 20 | 6.3 |
| II + III (in the same ratio as in compound I) | LD50 = 1 × (202+147) | ED50 = 1 × (25.6+18.7) | 7.9 |
| Prednisolone-21-p-[N-bis($\beta$-chloroethyl)-amino]-phenylbutyrate | LD50 = 1 × 261 | ED50 = 1 × 5.8 | 45 |
| Prednisolone-21-p-[N-bis($\beta$-chloroethyl)-amino]-phenylacetate | LD50 = 1 × 560 | ED50 = 1 × 27 | 21 |
| Chlorambucil | LD50 = 1 × 30 | ED50 = 1 × 4.3 | 7.1 |

$^{x}$T.I. = $\frac{LD50}{ED50}$

TABLE 3

| Compound | Harding-Passey Melanoma tumor Lethality (mg/kg) | Effect (mg/kg) | T.I.[x] |
|---|---|---|---|
| Prednisolone-21-p-[N-bis($\beta$-chloroethyl)-amino]-benzoate | LD50 = 11 × 20 | ED50 = 3.4 | 6.8 |
| Prednisone-21-p-[N-bis($\beta$-chloroethyl)-amino]-benzoate | LD50 = 11 × 97 | ED50 = 11 × 18 | 5.4 |
| Hydrocortisone-21-p-[N-bis($\beta$-chloroethyl)-amino]-benzoate | LD50 = 11 × 82 | ED50 = 11 × 19 | 4.3 |
| Prednisolone | LD50 = 11 × 600 | 11 × 243: no effect | <2.5 |
| Prednisolone-21-p-[N-bis($\beta$-chloroethyl)-amino]-phenylbutyrate | LD50 = 11 × 6.8 | ED50 = 11 × 3.1 | 2.2 |

$^{x}$T.I. = $\frac{LD50}{LD50}$

TABLE 4

| Compound | Walker 256 tumor Lethality (mg/kg) | Effect (mg/kg) | T.I.[x] |
|---|---|---|---|
| Prednisolone-21-p-[N-bis($\beta$-chloroethyl)-amino]-benzoate (I) | LD50 = 5 × 0 168 | ED50 = 5 × 9.6 | 18 |
| Prednisolone-21-p-[N-bis($\beta$-chloroethyl)-amino]-phenylbutyrate | LD50 = 5 × 32 | ED50 = 5 × 1.1 | 29 |
| Prednisolone (II) | LD50 = 5 × 650 | ED50 = 5 × 214 | 3.0 |
| p-[N-bis($\beta$-chloroethyl)-amino]-benzoic acid (III) | LD50 = 5 × 89 | ED50 = 5 × 13.4 | 6.6 |
| II + III (in the same ratio as in compound I) | LD50 = 5 × (81 + 59) | ED50 = 5 × (10.7 + 7.8) | 7.5 |

TABLE 4-continued

| Compound | Walker 256 tumor Lethality (mg/kg) | Effect (mg/kg) | T.I.[x) |
|---|---|---|---|
| [x)T.I. = LD50/ED50 | | | |

TABLE 5

| Tumor | Compound | Lethality (mg/kg) | Effect (mg/kg) | T.I.[x) |
|---|---|---|---|---|
| Hepatoma 130 | Chlorambucil | LD50 = 1 × 55 | ED50 > 1 × 31 | <1.8 |
| Hepatoma 130 | Prednisolone-21-4'-[p-/N-bis($\beta$-chloroethyl)-amino/-phenyl]-butyrate | LD50 = 1 × 380 | ED50 = 1 × 155 | 2.5 |
| Harding-Passey Melanoma | Chlorambucil | LD50 = 11 × 7.0 | ED50 = 11 × 2.3 | 3.0 |
| Harding-Passey Melamona | Prednisolone-21-4'-[p-/N-bis($\beta$-chloroethyl)-amino/-phenyl]-butrate | LD50 = 11 × 40 | ED50 = 11 × 6.0 | 6.7 |
| Walker 256 | Chlorambucil | LD50 = 5 × 13.5 | ED50 = 5 × 0.42 | 32 |
| Walker 256 | Prednisolone-21-4'-[p-/N-bis($\beta$-chloroethyl)-amino/-phenyl]butyrate | LD50 = 5 × 64 | ED50 = 5 × 1 | 64 |

[x)T.I. = LD50/ED50

We claim:
1. A pharmaceutical composition, comprising from about 0.01 to about 75 weight percent of a corticoid steroid 21-ester of the general formula

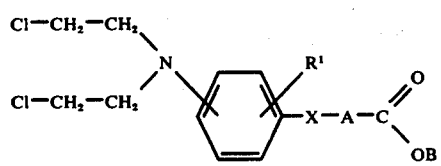

wherein $R^1$ is hydrogen, lower-alkyl, halogen or lower-alkoxy;
X is oxygen, sulphur or a monovalent carbon-carbon bond;
A represents the group

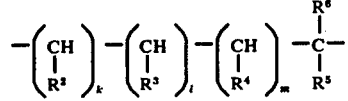

wherein $R^2$, $R^3$, $R^4$, $R^5$ and $R^6$ represent similar or dissimilar atoms or atom groups selected from the group consisting of hydrogen and lower-alkyl, and wherein $R^6$ can also be selected from the group consisting of amino and lower-alkanoylamino, in which case $R^5$ is hydrogen,
wherein k, l and m are integers having a value of zero or one, or A together with X (—X—A) represents a monovalent carbon-carbon bond; and B represents the radical of a corticoid steroid of the formula

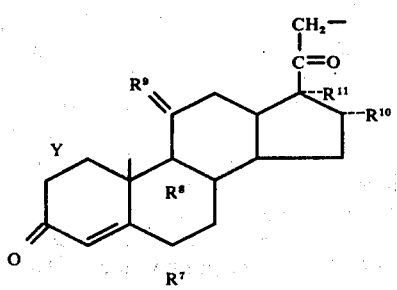

wherein Y is a carbon-carbon single bond or a carbon-carbon double bond;
$R^7$ is hydrogen, methyl or F;
$R^8$ is hydrogen or F;
$R^9$ is oxygen or the group

$R^{10}$ is hydrogen, methyl or hydroxy;
$R^{11}$ is hydrogen or hydroxy; and wherein $R^{10}$ and $R^{11}$ together can form an alkylidenedioxy group and a pharmaceutical carrier.
2. A pharmaceutical composition as described in claim 1 wherein the corticoid steroid 21-ester has the formula

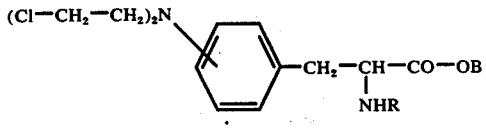

wherein B is the radical of a corticoid steroid selected from the group consisting of cortisone, hydrocortisone, prednisone, and prednisolone, and wherein R is hydrogen or lower-alkanoyl having up to and including four carbon atoms.
3. A composition as described in claim 1 wherein the corticoid steroid radical B is the radical of a compound selected from the group consisting of pregn-4-en-17$\alpha$, 21-diol-3, 11, 20-trion; pregn-4-en-11$\beta$, 17$\alpha$, 21-triol-3,20-dion; pregn-4-en-11$\beta$, 21-diol-3,20-dion; pregn-4-en-21-ol-3,11,20-trion; pregna-1,4-dien17$\alpha$, 21-diol-3, 11,20-trion; pregna-1,4-dien-11$\beta$,17$\alpha$,21-triol-3, 20-dion; 6$\alpha$-methylpregna-1,4-dien-11$\beta$,17$\alpha$,21-triol-3,20-dion; 9$\alpha$-fluor-pregn-4-en-11$\beta$,17$\alpha$, 21-triol-3,20-dion; 6$\alpha$,9$\alpha$-difluor-pregn-1,4-dien-11$\beta$,16$\alpha$,17$\alpha$,21-tetrol-3,20-dion; 16$\alpha$-methyl-9$\alpha$-fluor-pregna-1,4-dien-11$\beta$,17$\alpha$, 21-triol-3,20-dion; 9$\alpha$-fluor-16$\beta$-methylprednisolone; 9$\alpha$-fluor-16$\alpha$-hydroxyprednisolone; 16-methylenprednisolone; 6$\alpha$, 9$\alpha$-di-fluor-11$\beta$,17$\alpha$,21-trihydroxy-16$\alpha$-methylpregnadien-(1,4)-dion-(3,20) 6$\alpha$,9$\alpha$-difluor-11$\beta$,21-dihydroxy-3,20-dioxo-16$\alpha$,17$\alpha$-isopropyliden-dioxypregnadien-(1,4); 6$\alpha$,9$\alpha$-difluor-16$\alpha$,hydroxyprednisoloneacetonid- (16,17); 6α-fluor-11β,21-dihydroxy-16α-methyl-3,20-dioxypregnadien-(1,4); 6α-fluor-16α-hydroxyhydrocortisone-16,17-acetonid; and 6α-methylprednisolone.

4. The composition in accordance with claim 1 wherein said corticoid steroid ester is present in an amount in the range from about 0.05 to about 15 weight percent.

5. The composition of claim 1 wherein the corticoid steroid 21-ester is hydrocortisone-21-p-/N-bis(β-chloroethyl)-amino/-benzoate.

6. The composition of claim 1 wherein the corticoid steroid 21-ester is prednisone-21-p-/N-bis(β-chloroethyl)-amino/-benzoate.

7. The composition of claim 1 wherein the corticoid steroid 21-ester is prednisolone-21-p-/N-bis(β-chloroethyl)-amino/-benzoate.

8. The composition of claim 1 wherein the corticoid steroid 21-ester is prednisolone-21-p-/N-bis(β-chloroethyl)-amino/-phenylacetate.

9. The composition of claim 1 wherein the corticoid steroid 21-ester is prednisolone-21-4'-[p-/N-bis-(β-chloroethyl)-amino/-phenyl]-butyrate.

10. The composition of claim 1 wherein the corticoid steroid 21-ester is hydrocortisone-21-4'-[p-/N-bis(β-chloroethyl)-amino/-phenyl]-butyrate.

11. The composition of claim 1 wherein the corticoid steroid 21 -ester is prednisolone-21-3'-[N-bis-(β-chloroethyl)amino]-4'-methylbenzoate.

12. The composition of claim 1 wherein the corticoid steroid 21-ester is prednisolone-21-3'- p-[N-bis-(β-chloroethyl)-amino]-phenyl -2'-acetamidopropionate.

13. The composition of claim 1 wherein the corticoid steroid 21-ester is prednisolone-21-3'- p-[N-bis-(β-chloroethyl)-amino]-phenyl -2'-aminopropionate.

14. The composition of claim 1 wherein the corticoid steroid 21-ester is hydrocortisone-21-3'- p-[N-bis-(β-chloroethyl)-amino]-phenyl 2'-aminopropionate.

15. The composition of claim 1 wherein the corticoid steroid 21-ester is prednisone-21-4'-[p-/N-bis(β-chloroethyl)-amino/-phenyl]-butyrate.

16. The composition of claim 1 wherein the corticoid steroid 21-ester is prednisolone-21-4'-(p-(N-bis(β-chloroethyl)-amino)-phenyl)-acetate.

17. A method for the palliative treatment of tumors in a living animal which comprises administering to said animal an amount of a corticoid steroid 21-ester of the general formula

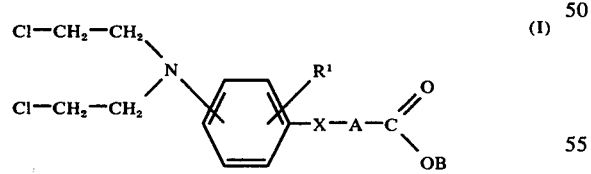

wherein R¹ is hydrogen, lower-alkyl, halogen or lower-alkoxy;

X is oxygen, sulphur or a monovalent carbon-carbon bond;

A represents the group

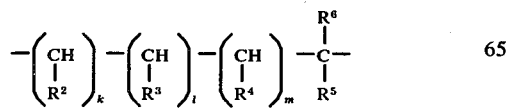

wherein R², R³, R⁴, R⁵ and R⁶ represent similar or dissimilar atoms or atom groups selected from the group consisting of hydrogen and lower-alkyl, and wherein R⁶ can also be selected from the group consisting of amino and lower-alkanoylamino, in which case R⁵ is hydrogen, wherein k, l and m are integers having a value of zero or one, or A together with X (—X—A) represents a monovalent carbon-carbon bond; and B represents the radical of a corticoid steroid of the formula

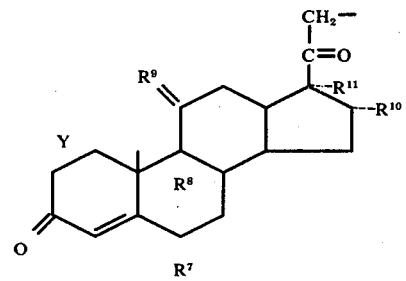

wherein Y is a carbon-carbon single bond and a carbon-carbon double bond;

R⁷ is hydrogen, methyl or F;
R⁸ is hydrogen or F;
R⁹ is oxygen or the group

R¹⁰ is hydrogen, methyl or hydroxy;
R¹¹ is hydrogen or hydroxy; and
wherein R¹⁰ and R¹¹ together can form an alkylidenedioxy group which is effective for said purpose.

18. The method as described in claim 17 wherein the corticoid steroid 21-ester administered is a steroid 21-ester of claim 17 having the formula

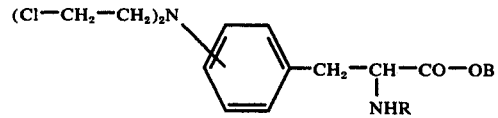

wherein B is the radical of a corticoid steroid selected from the group consisting of cortisone, hydrocortisone, prednisone, and prednisolone, and wherein R is hydrogen or lower-alkanoyl having up to and including four carbon atoms.

19. The method as described in claim 17 wherein the corticoid steroid 21-ester administered is a compound of claim 17 wherein the steroid radical B is the radical of a compound selected from the group consisting of pregn-4-en-17α,21-diol-3,11,20-trion; pregn-4-en-11β,17α,21-triol-3,20-dion; pregn-4-en-11β, 21-diol-3,20-dion; pregn-4-en-21-ol-3,11,20-trion; pregna-1,4-dien-17α,21-diol-3, 11,20-trion; pregna-1,4-dien-11β,17α,21-triol-3, 20-dion; 6α-methylpregna-1,4-dien-11β,17α,21-triol-3,20-dion; 9α-fluor-pregn-4-en-11β,17α, 21-triol-3,20-dion; 6α,9α-difluor-pregn-1,4-dien-11β,16α,17α,21-tetrol-3,20-dion 16α-methyl-9α-fluor-pregna-1,4-dien-11β, 17α,21-triol-3,20-dion; 9α-fluor-16β-methylprednisolone; 9α-fluor-16α-hydroxyprednisolone; 16-methylenprednisolone; 6α,9α-di-fluor-11β,17α,21-trihydroxy-16α-methylpregnadien-(1,4)-dion-(3,20) 6α,9α-difluor-11β,21-dihydroxy-3,20-dioxo-16α,17α-isopropyliden-dioxypregnadien-(1,4); 6α,9α-difluor-16α,hydroxy-prednisoloneacetonid-(16,17); 6α-fluor-11β,21-dihydroxy-16α-methyl-3,20-dioxopregnadien-(1,4); 6α-fluor-16α-hydroxyhydrocortisone-16,17-acetonid; and 6α-methylprednisolone.

20. The method in accordance with claim 17 wherein said corticoid steroid ester is administered in a dosage in the range from about 2 to about 100 milligrams daily.

21. The method of claim 17 wherein the corticoid steroid 21-ester administered is hydrocortisone-21-p-/N-bis (β-chloroethyl)-amino/-benzoate.

22. The method of claim 17 wherein the corticoid steroid 21-ester administered is prednisone-21-p-/N-bis(β-chloroethyl)-amino/-benzoate.

23. The method of claim 17 wherein the corticoid steroid 21-ester administered is prednisolone-21-p-/N-bis (β-chloroethyl)-amino/-benzoate.

24. The method of claim 17 wherein the corticoid steroid 21-ester administered is prednisolone-21-p-/N-bis(β-chloroethyl)-amino/-phenylacetate.

25. The method of claim 17 wherein the corticoid steroid 21-ester administered is prednisolone-21-4'-[p-/N-bis-(β-chloroethyl)-amino/-phenyl]-butyrate.

26. The method of claim 17, wherein the corticoid steroid 21-ester administered is hydrocortisone-21-4'-[p-/N-bis (β-chloroethyl)-amino/-phenyl]-butyrate.

27. The method of claim 17 wherein the corticoid steroid 21-ester administered is prednisolone-21-3'-[N-bis-(β-chloroethyl)amino]-4'-methylbenzoate.

28. The method of claim 17 wherein the corticoid steroid 21-ester administered is prednisolone-21-3'- p-[N-bis-(β-chloroethyl)-amino]-phenyl -2'-acetamidopropionate.

29. The method of claim 17 wherein the corticoid steroid 21-ester administered is prednisolone-21-3'- p-[N-bis-(β-chloroethyl)-amino]-phenyl -2'-aminopropionate.

30. The method of claim 17 wherein the corticoid steroid 21-ester administered is hydrocortisone-21-3'- p-[N-bis-(β-chloroethyl)-amino]-phenyl -2'-aminopropionate.

31. The method of claim 17 wherein the corticoid steroid 21-ester administered is prednisone-21-4'-[p-/N-bis(β-chloroethyl)-amino/-phenyl]-butyrate.

32. The method as described in claim 17 wherein the corticoid steroid 21-ester administered is prednisolone-21-4'-(p-(N-bis(β-chloroethyl)-amino)-phenyl)-acetate.

* * * * *

UNITED STATES PATENT OFFICE
CERTIFICATE OF CORRECTION

Patent No. 4,029,778          Dated June 14, 1977

Inventor(s) Hans Jacob Fex, Knut Fertil Högberg & Imre Konyves

It is certified that error appears in the above-identified patent and that said Letters Patent are hereby corrected as shown below:

Col. 1, Line 61; Change "of compounds of wherein" to read ---of compounds wherein---

Col. 1, Line 66; Change "meaning as" to read ---meaning an---

Col. 5, Line 24; Change "$(\alpha)_D 24$ C=" to read ---$(\alpha)_D^{24°}$ C=---

Col. 5, Line 53; Change "$(\alpha)_D 24$ C=" to read ---$(\alpha)_D^{24°}$ C=---

Col. 5, Line 62; Change "$(\alpha)_D 24$ C=" to read ---$(\alpha)_D^{24°}$ C=---

Col. 6, Line 3 ; Change "$(\alpha)_D 24$ C=" to read ---$(\alpha)_D^{24°}$ C=---

Col. 6, Line 24; Change "$(\alpha)_D 24$ C=" to read ---$(\alpha)_D^{24°}$ C=---

Col. 7, Line 11; Change "$(\alpha)_D 24$ C=" to read ---$(\alpha)_D^{24°}$ C=---

Col. 7, Line 25; Change "$(\alpha)_D 24$ C=" to read ---$(\alpha)_D^{24°}$ C---

Col. 7, Line 52; Change "$(\alpha)_D 24$ C=" to read ---$(\alpha)_D^{24°}$ C---

Col. 8, Line 50; Change "$(\alpha)_D 24$ C=" to read ---$(\alpha)_D^{24°}$ C---

Col. 9, Line 64; Change "reactionmixture" to read ---reaction mixture---

Col.10, Line 4; Change "$(\alpha)_D 24$ C=" to read ---$(\alpha)_D^{24°}$ C---

UNITED STATES PATENT OFFICE
CERTIFICATE OF CORRECTION

Patent No. 4,029,778        Dated June 14, 1977

Inventor(s) Hans Jacob Fex, Knut Fertil Högberg and Imre Konyves

It is certified that error appears in the above-identified patent and that said Letters Patent are hereby corrected as shown below:

Col.10, Line 22; Change "$(\alpha)^{24}_D$ C=" to read ---$(\alpha)^{24°}_D$ C= ---

Col.11, Table 3; "x)T.I.=$\frac{LD50}{LD50}$" to read ---x)T.I. = $\frac{LD50}{ED50}$"

Col.12, Table 4; "LD50 = 5 x0 168" to read ---LD50 = 5 x 168---

Col.13, Line 57; Change " 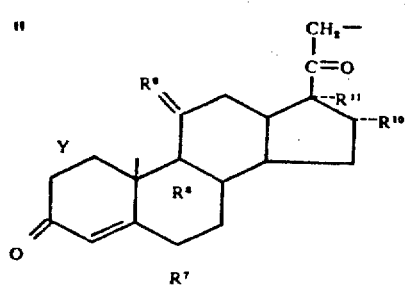 " to read

--- 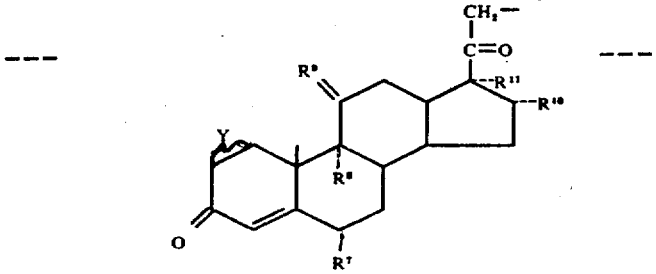 ---

UNITED STATES PATENT OFFICE
CERTIFICATE OF CORRECTION

Patent No. 4,029,778        Dated June 14, 1977

Inventor(s) Hans Jacob Fex, Knut Fertil Högberg & Imre Konyves

It is certified that error appears in the above-identified patent and that said Letters Patent are hereby corrected as shown below:

Col. 15, Line 31-32, Change " 21-3'-p-[N-bis-(β-chloroethyl)-amino]-phenyl-2' to read --- 21-3'-/p-[N-bis-(β-chloroethyl)-amino]-phenyl/-2'---

Col. 15, Line 34-35, Change "21-3'- p-[N-bis-(β-chloroethyl)-amino]-phenyl -2'-" to read ---21-3'-/p-[N-bis-(β-chloroethyl)-amino]-phenyl/-2'- ---

Col. 15, Line 38-39, Change "21-3'-p-[N-bis(β-chloroethyl)-amino]-phenyl-2'-aminopropionate." to read --- 21-3'-/p-[N-bis-(β-chloroethyl)-amino]-phenyl/-2'-aminopropionate

UNITED STATES PATENT OFFICE
CERTIFICATE OF CORRECTION

Patent No. 4,029,778          Dated June 14, 1977

Inventor(s) Hans Jacob Fex, Knut Fertil Högberg & Imre Konyves

It is certified that error appears in the above-identified patent and that said Letters Patent are hereby corrected as shown below:

Col. 16, Line 12; Change " 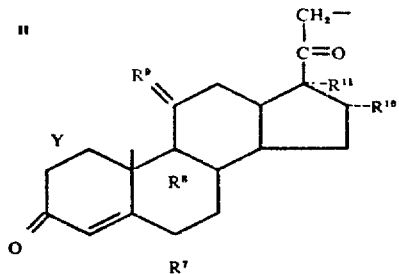 " to read

--- 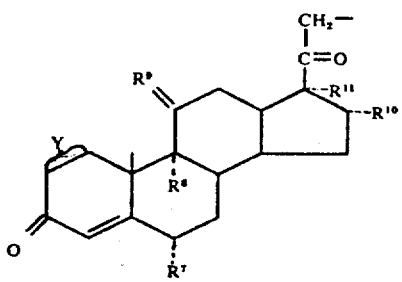 ---

Col. 16, Line 25; Change "and a" to read ---or a ---

Col. 16, Line 37; Change "group which" to read ---group,which---

Col. 18, Line 11-12; Change "21-3'-p-[N-bis-(β-chloroethyl)-amino]-phenyl -2' " to read ---21-3'-/p-[N-bis-(β-chloroethyl)-amino]-phenyl/-2'---

Col. 18, Line 15-16; Change "21-3'-p-[N-bis-(β-chloroethyl)-amino]-phenyl -2'-aminopropionate" to read ---21-3'-/p-[N-bis-(β-chloroethyl)-amino]-phenyl/2'aminopropionate.---

Col. 18, Line 19-20; Change "21-3'-p-/N-bis-(β-chloroethyl)-amino/-phenyl-2'" to read ---21-3'-/p-/N-bis-(β-chloroethyl)-amino/-phenyl/-2'---

UNITED STATES PATENT OFFICE
CERTIFICATE OF CORRECTION

Patent No. 4,029,778　　　　　　Dated June 14, 1977

Inventor(s) Hans Jacob Fex, Knut Fertil Hogberg & Imre Konyves

It is certified that error appears in the above-identified patent and that said Letters Patent are hereby corrected as shown below:

Col. 10, Line 4; Change "$(\alpha)_D^{24}\ ^C=+153°(C=1.03\ in\ CHCl_3)$"

to read ---$(\alpha)_D^{24°C}=+153°(c=1.03\ in\ CHCl_3)$---

Col. 10, Line 22; Change "$(\alpha)_D^{24}\ ^C=+92.9(C=1.06\ in\ CHCl_3)$"

to read ---$(\alpha)_D^{24°C}=+92.9(c=1.06\ in\ CHCl_3)$---

Signed and Sealed this

*Sixth* Day of *December 1977*

[SEAL]

*Attest:*

RUTH C. MASON　　　　　LUTRELLE F. PARKER
*Attesting Officer*　　　　*Acting Commissioner of Patents and Trademarks*